(12) United States Patent
Cash et al.

(10) Patent No.: US 7,211,388 B2
(45) Date of Patent: May 1, 2007

(54) METHOD FOR PROFILING AND IDENTIFYING PERSONS BY USING DATA SAMPLES

(75) Inventors: Howard Cash, Ann Arbor, MI (US); Simon Mercer, Ann Arbor, MI (US); Jonathon Hoyle, Ann Arbor, MI (US); Lucy Hadden, Ann Arbor, MI (US); Amy Sutton, Ypsilanti, MI (US); David Relyea, Redmond, WA (US); William Wake, Richmond, VA (US); Matthew Smith, Ann Arbor, MI (US); Tom Kubit, Sylvania, OH (US); Greg Poth, Ann Arbor, MI (US); Anna Korn, St. Louis, MO (US); Anna Khizhnyak, Rockville, MD (US); Tracy Beeson, Ann Arbor, MI (US)

(73) Assignee: Gene Codes Forensics, Inc., Ann Arbor, MI (US)

( * ) Notice: Subject to any disclaimer, the term of this patent is extended or adjusted under 35 U.S.C. 154(b) by 15 days.

(21) Appl. No.: 10/736,823

(22) Filed: Dec. 15, 2003

(65) Prior Publication Data

US 2004/0126803 A1 Jul. 1, 2004

Related U.S. Application Data

(60) Provisional application No. 60/433,123, filed on Dec. 13, 2002.

(51) Int. Cl.
  *C12Q 1/68* (2006.01)
  *G01N 1/37* (2006.01)
(52) U.S. Cl. ............................. 435/6; 702/19; 702/20; 436/94
(58) Field of Classification Search .................. 702/19, 702/20; 435/6
  See application file for complete search history.

(56) References Cited

U.S. PATENT DOCUMENTS

| 5,364,759 | A | 11/1994 | Caskey et al. |
| 5,844,554 | A * | 12/1998 | Geller et al. ................. 715/744 |
| 6,251,592 | B1 | 6/2001 | Tang et al. |
| 6,642,946 | B1 * | 11/2003 | Janes et al. .................. 715/854 |
| 2002/0010552 | A1 | 1/2002 | Rienhoff et al. |
| 2003/0175701 | A1 | 9/2003 | Griffiths et al. |
| 2003/0225530 | A1 * | 12/2003 | Lowe et al. ................... 702/20 |
| 2004/0186846 | A1 * | 9/2004 | Birdwell et al. ............. 707/101 |

OTHER PUBLICATIONS

"STR profiling", http://www.sciencemuseum.org.uk/exhibitions/genes/127.asp, Science Museum, (date unknown—cited by PCT office in Written Opinion).

Ruitberg et al; STRBase: a short tandem repeat DNA database for the human identity testing community; Nucleic acids research; 2001; vol. 29, No. 1; pp. 320-322.

Radtkey et al; Rapid, high fidelity analysis of simple sequence repeats on an electronically active DNA microshop; Nucleic Acides Research; 2000; vol. 28, No 7; pp. i-iv.

* cited by examiner

*Primary Examiner*—Michael Borin
(74) *Attorney, Agent, or Firm*—Baker & McKenzie LLP (57) ABSTRACT

A method for profiling and identifying persons by using data samples provides a collapsed list of one or more aggregated matching samples having consistent STR profiles. Each of the one or more aggregated matching samples are presented on a one-line display, the one-line display having a composite profile representing consensus of all STR profiles in an associated aggregate matching sample. The one-line display of an aggregated matching sample may be expanded, and the expanded one-line display provides a view of all member samples in the aggregated matching sample. A method for aggregating samples from a plurality of disparate samples, and combining the aggregated samples is also provided.

17 Claims, 11 Drawing Sheets

| ID | RM | Likelihood | I | # MjSn | Gen | D3S1358 | vWA | FGA | D8S1179 | D21S11 | D18S51 | D5S818 | D13S317 | D7S820 | D16S539 | TH01 | TPOX | CSF1PO | Penta D | Penta E |
|---|---|---|---|---|---|---|---|---|---|---|---|---|---|---|---|---|---|---|---|---|
| RM#1019 (3) | | | | | | | | | | | | | | | | | | | | |
| S2-00039-21 | 1019 | 2.3E+016 | 0 | 13 | XX | 14/16 | 17 | neg | 12/14 | 30 | 12/21 | 8/12 | 12 | 9/11 | 13 | 9/9.3 | 8/10 | 12 | | |
| BODE-DM0106884 | | 2.3E-016 | | 7 | XX | 14/16 | 17 | neg | 12/14 | 30 | 12/21 | 8/12 | 12 | 9/11 | 13 | 9/9.3 | 8/10 | 12 | | |
| VIRT-DM0107078 | | 1.2E-008 1.2E-008 | | 10 | XX | 14/16 | 17 | neg | 12/14 | neg | neg | 8/12 | neg | neg | neg | 9/9.3 | 8/10 | neg | | |
| | | 2.7E-012 2.7E-012 | | | | | | | | | | | | | | | | | | |
| AS009676 (4) | | 2.4E+015 | 0 | 8 | XX | 14/16 | 17 | 23/26 | 12/14 | 30 | 12/21 | 8/12 | 12 | neg | 12/13 | 9/9.3 | 8/10 | neg | | |
| BODE-DM0106841 | | 5.6E-008 | | 7 | XX | 14/16 | 17 | neg | 12/14 | neg | neg | 8/12 | 12 | neg | 12/13 | 9/9.3 | 8/10 | neg | | |
| BODE-DM0106884 | | 1.2E-008 | | 10 | XX | 14/16 | 17 | neg | 12/14 | 30 | 12/21 | 8/12 | 12 | neg | 12/13 | 9/9.3 | 8/10 | neg | | |
| VIRT-DM0107078 | | 2.7E-012 | | 11 | XX | 14/16 | 17 | 23/26 | 12/14 | 30 | neg | 8/12 | 12 | neg | 12/13 | 9/9.3 | 8/10 | neg | | |
| VIRT-DM0114805 | | 1.2E-013 | | | | | | | | | | | | | | | | | | |

Comparing Candidate Samples to Aggregates

| | | | | | | |
|---|---|---|---|---|---|---|
| MergeCount = 0 | | | | | | 602 |
| Place candidate aggregates into bins by size | | | | | | 604 |
| For each size bin SB (in order of descending size) | | | | | | 606 |
| | Calculate signatures using SB and all target aggregates | | | | | 608 |
| | Place contents of SB into candidate bins by signature | | | | | 610 |
| | For each candidate aggregate signature bin CAB | | | | | 612 |
| | | For each target aggregate signature bin TAB | | | | 614 |
| | | | If signature of CAB matches signature of TAB | | | 616 |
| | | | | For each candidate aggregate CA in CAB | | 618 |
| | | | | | Merged = false | 620 |
| | | | | | For each target aggregate TA in TAB | 622 |
| | | | | | | If CA's profile matches TA's profile | 624 |
| | | | | | | Merge CA into TA | 626 |
| | | | | | | Merged = true | 628 |
| | | | | | | MergeCount = MergeCount + 1 | 630 |
| | | | | If Merged = false | | | 632 |
| | | | | | Put candidate aggregate into proper target aggregate bin by signature | | 634 |
| | If MergeCount > 0 | | | | | 636 |
| | | Move target aggregates to candidate aggregates | | | | 638 |
| Repeat until MergeCount = 0 | | | | | | 640 |

Merging Aggregates

| 704 | 706 | 708 | 710 |
|---|---|---|---|
| 5372 | 53F2 | 537A | 53F3 |
| Exact match | Match ("F" matches anything) | Mismatch | Mismatch |

(This assumes no mismatches are allowed.)

702: 5372

Each hex digit represents the normalized low allele value of some of the sample's markers. The specific markers used and number of markers used are determined by the Signature Calculator.

Signature Comparison – Allelic Dropout is a Mismatch

| 804 | 806 | 808 | 810 |
|---|---|---|---|
| 77 | BB | 7C | FF |
| Match (7's match) | Match (B's match) | Mismatch | Match (F's match anything) |

This comparison table represents the comparison of corresponding portions of two signatures. It is repeated for the entire signature. (This assumes no mismatches are allowed.)

812: 58457B

Each marker is represented by its normalized low and high allele values. The markers used are determined as above.

Signature Comparison – Allelic Dropout is not a Mismatch

METHOD FOR PROFILING AND IDENTIFYING PERSONS BY USING DATA SAMPLES

CROSS-REFERENCE TO RELATED APPLICATIONS

This application claims the benefit of U.S. Provisional Application No. 60/433,123, filed Dec. 13, 2002, the entire disclosure of which is incorporated herein by reference.

TECHNICAL FIELD

The present application relates to profiling and identifying persons by using data such as DNA samples.

BACKGROUND

Large-scale DNA triage, for example, profiling or identifying a mass number of persons from partial or incomplete DNA samples is difficult to address in the world of forensic biology. For example, in a case of mass destruction, thousands of victim STR profiles (many of them partial due to sample degradation) need to be compared to each other and to reference samples to identify reported missing victims. Accordingly, an efficient method for identifying persons in such cases as mass destructions is needed.

SUMMARY

A method for profiling and identifying persons by using data samples provides a collapsed list of one or more aggregated matching samples having consistent STR profiles. Each of the one or more aggregated matching samples are presented on a one-line display, the one-line display having a composite profile representing consensus of all STR profiles in an associated aggregate matching sample. The one-line display of an aggregated matching sample may be expanded, and the expanded one-line display provides a view of all member samples in the aggregated matching sample. A method for aggregating samples from a plurality of disparate samples, and combining the aggregated samples is also provided.

BRIEF DESCRIPTION OF THE DRAWINGS

FIG. 1C illustrates a window having all the aggregates with all STR matches.

DETAILED DESCRIPTION

The method of the present disclosure in one aspect provides results of comparison of many STR profiles and reference samples organized into a 'collapsed' list of aggregated matching samples having consistent STR profiles. Aggregates of STR samples are displayed on one line with a composite profile representing the consensus of all of the STR results for that aggregate's samples. Each of these aggregates may be expanded to view all member samples. All potential matches for a sample are presented, for example, those that meet a user-defined threshold of specificity, so it is possible for any given sample to belong to more than one aggregate in the list. These samples are prominently marked with a yellow ambiguity flag so that when these samples based on DNA information are identified all of their potential matches are examined. Configurable STR Profile comparison criteria, STR data displayed in expandable composite profiles, data flags on ambiguous samples, and virtual profiles for multiple assays on the same sample create a data presentation which allows the forensic biologist to quickly locate samples that have a putative identification match and make a positive DNA identification with confidence that they have reviewed any possible conflicting data. Aspects of the method disclosed in the present application are embodied in a software system referred to as M-FISys.

Figure 1A:
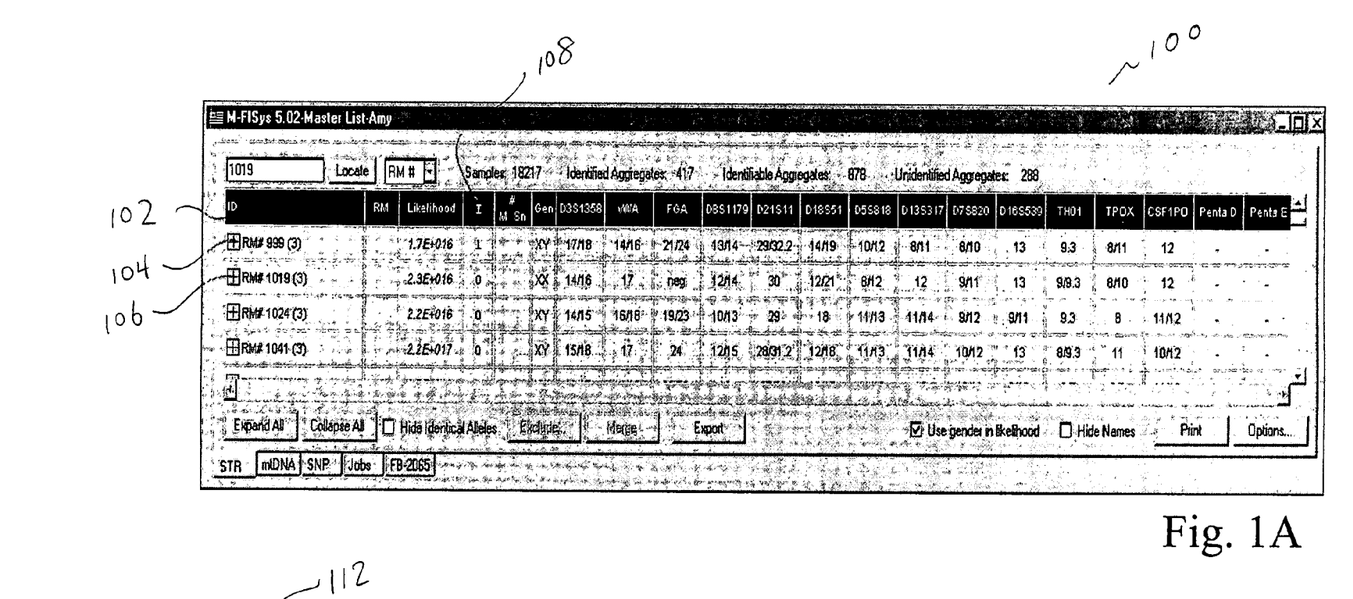
FIG. 1A is a window illustrating the organized collapsed master aggregate list in one embodiment.

FIG. 1A is a window illustrating the organized collapsed master aggregate list in one embodiment. The collapsed master aggregate list 100 lists unidentified aggregates 102. Aggregate RM#999 (Reported Missing #999) 104 has a 1 in the 'I' column 108 indicating that 1 victim sample has already been identified as Reported Missing person 999. Aggregate RM#1019, however, does not contain any identified victim samples as indicated by '0' in the 'I' column 108.

Figure 1B:
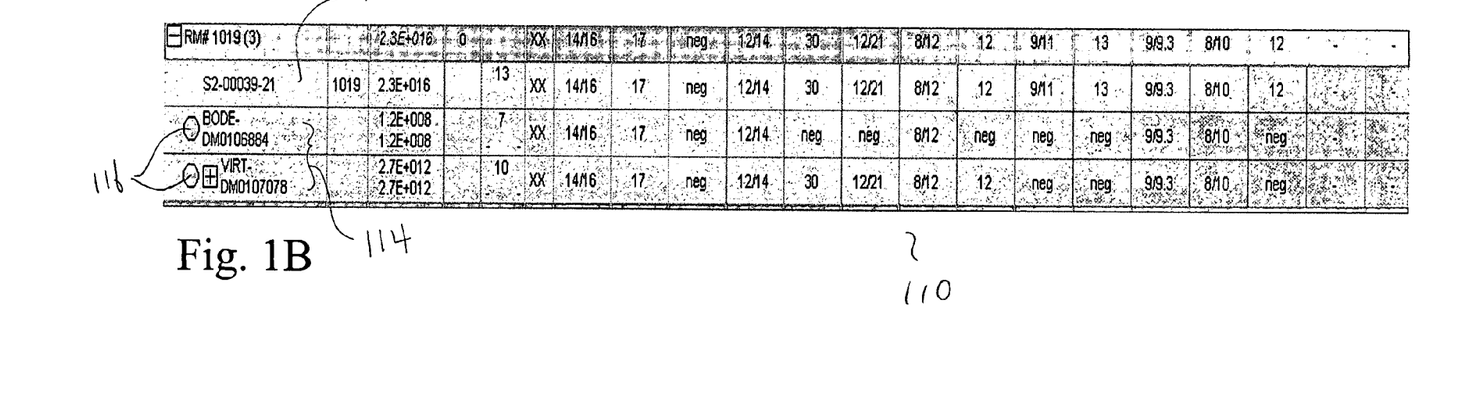
FIG. 1B is a window showing the expanded aggregate.

Clicking on the '+' next to RM#1019 106 expands that aggregate. FIG. 1B is a window showing the expanded aggregate. The expanded aggregate 110 contains a Personal Reference sample for Reported Missing person 1019 (e.g., STR profile from the victim's toothbrush) 112, and two victim samples 114 marked with yellow ambiguity flags 116 indicating that these samples match more than one aggregate.

Each ambiguous sample 114 may be examined, for example, by choosing the 'All STR Matches' command from a pull down menu of the window, and inspecting all of the aggregates that have consistent STR profiles. FIG. 1C illustrates a window having all the aggregates with all STR matches. In this example, both of the ambiguous victim samples 116 118 are in the same two aggregates, RM# 1019 120 and AS009676 122 (note that this aggregate contains no reference sample, and thus has no RM number associated with it). The STR profiles for these two aggregates 120 122 differ at two loci, FGA 124 and D16S539 126. Only D16S539 126 has inconsistent STR data: a homozygous 13 in the S2 sample versus a heterozygous 12/13 in the two victim samples in AS009676.

Figure 1D:
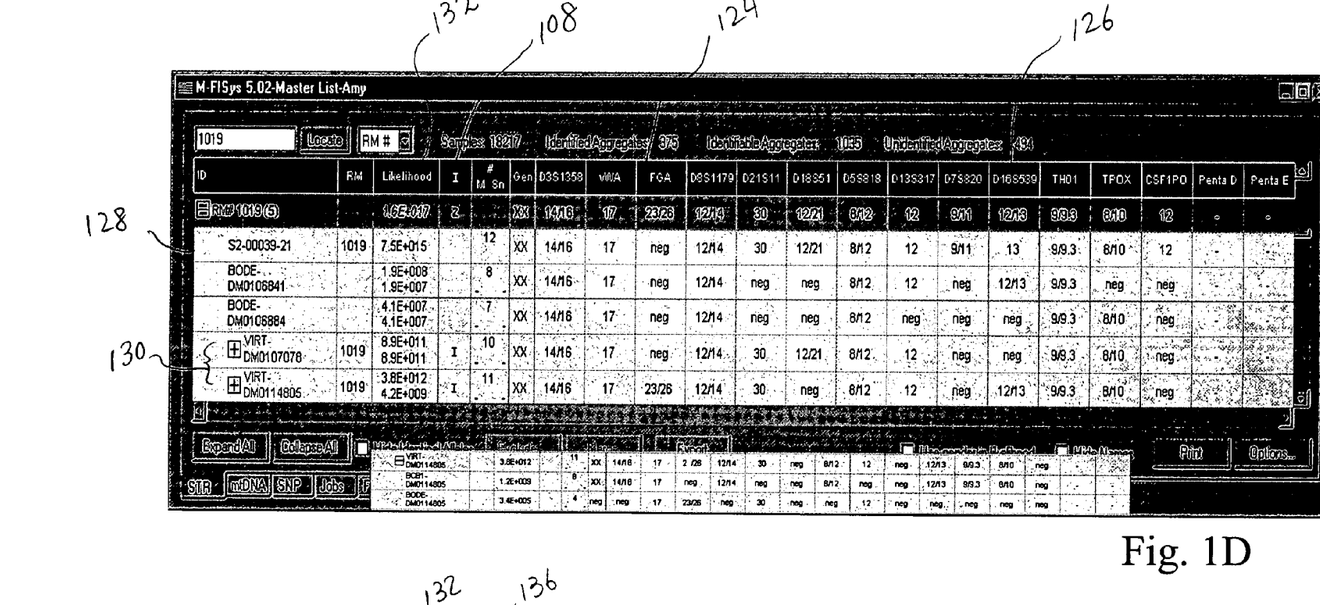
FIG. 1D illustrates a window showing a merged aggregate in one embodiment.

Each ambiguous sample may be resolved by either merging the aggregates into one, or excluding the sample from all but one aggregate. FIG. 1D illustrates a window showing a merged aggregate. In this example, the forensic biologist examined the raw experimental data for these samples and determined that the sample S2-00039-21 128 had allelic dropout at locus D16S539 and therefore, there was no discrepancy between the two aggregates. In this case, a 'Merge' command may be used to combine the aggregates into one to identify two of the victim samples 130. Note that RM#1019 now lists 2 in the 'I' column 108 and the composite STR profile on the gray line has been updated to reflect the new contents of the aggregate-FGA 124 is now 23/26 and D16S539 126 is now 12/13.

Two of the four victim samples in the example shown in FIG. 1D are still unidentified. These two samples do not meet the likelihood threshold to support identification. Victim samples have two likelihood numbers in the 'Likelihood' column 132. The top number is the most common likelihood for that sample's STR profile across four different populations-African, Asian, Caucasian, and Hispanic. The bottom number is the likelihood of the STR profile for loci shared in common with the Personal Effect Sample. It is this number that must be high enough to allow an identification. In this example, $2 \times 10^9$ is the cutoff. Both of the identified samples are 'Virtual Samples'. Highly degraded data samples, for example, those collected from a mass destruction site, may be assayed more than once in an attempt to generate more STR data. Samples with multiple experimental runs are grouped into virtual samples by M-FISys to create a virtual STR profile representing the results of all runs.

Figure 1E:
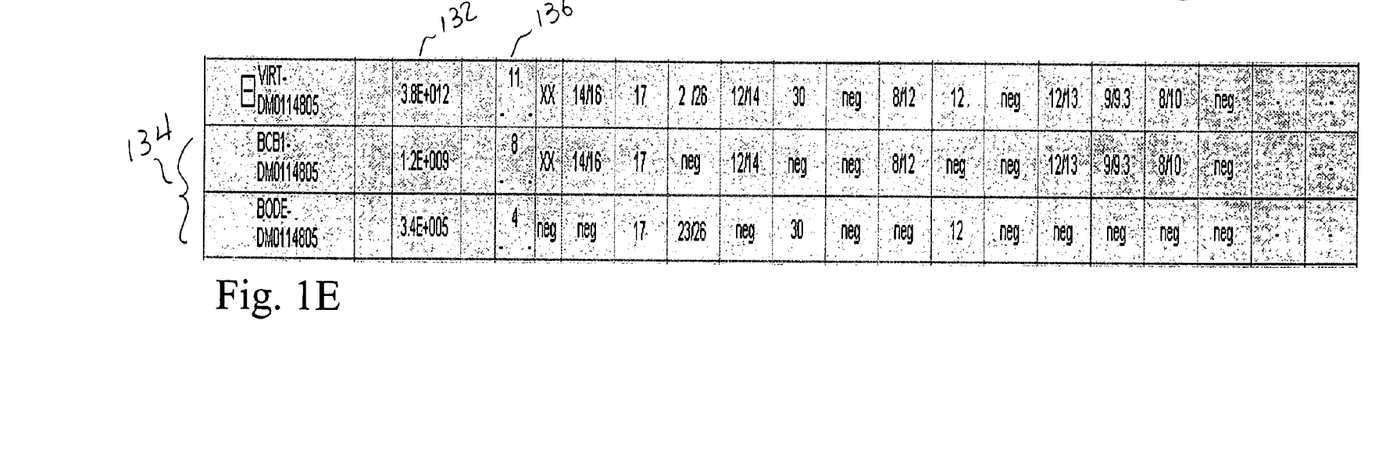
FIG. 1E illustrates expanded virtual sample in one embodiment.

FIG. 1E illustrates an expanded virtual sample in one embodiment. Clicking on the '+' next to VIRT-DM0114805 130 expands the virtual sample, which in this example, shows two experimental results 134, neither of which has a likelihood high enough to support identification. In one run, BODE-DM0114805 134, only 4 loci 136, returned any results. A second assay on this same physical sample, BCB1-DM0114805 134, returned 8 loci 136, filling in many of the holes in the STR profile. This new virtual profile has 11 loci, and taken together have a likelihood of $3.8 \times 10^{12}$ 132, high enough to be identified.

In the example shown in FIGS. 1A–1E, the ambiguous samples marked with yellow flag '●' were resolved by merging the two aggregates. Ambiguous samples may also be resolved by excluding the sample from all but one of the aggregates. In twin cases, for instance, one may expect a sample's STR profile to match a personal effect from both twins but one may know which twin is correct on the basis of other evidence. If other evidence exists to support one ID over another (information from the scene, or dental x-rays, etc.), then the sample can be 'Excluded' from belonging to an erroneous RM identity. Thus, an 'Exclude' command may be used to manually override matches that M-FISys has made on the basis of STR data alone.

The criteria governing whether or not a sample matches any aggregate are configurable. The settings result in match criteria that range from very permissive, allowing samples with low partial STR results to be added to aggregates, to very stringent, allowing only exact profile matches for high quality data.

Examples of methods that may be used to define a match in the M-FISys comparison settings include Use Match Count and Use Likelihood of Shared Loci. These methods may be used alone or in combination to define a match. In addition, other known methods may also be used to define a match, thus, the methods shown here are for illustrative purposes only and need not be limited to such.

In Use Match Count, required matches are the number of STR loci that samples share in common in order to be aggregated together. For example, sample 1 has results for 14 of the 15 STR loci and sample 2 has results for 12 loci. The two samples share 11 loci in common. If the number of required matches is 11, then M-FISys will aggregate the samples together providing all 11 loci have the same allele results. If the number of required matches is set to 13, then it doesn't matter if the 11 they share in common are exactly the same, because they are two loci short of meeting the match criteria. If either of the two alleles for a given locus differs between samples, then they do not match.

Allowed discrepancies may make certain allowances in comparison criteria. For example, the requirements for making a match may be set to allow 1 allele result at one locus to differ within an aggregate. Setting the mismatch allowance to 1 enables the user to relax the stringency of the comparison to allow for a minor experimental error or mutation. Displaying aggregates made under these comparison conditions directs the user to re-examine a sample that matches 'all but one' in order to discover these errors that otherwise would have prevented an identification of that sample.

When the Use Likelihood method is chosen, samples whose shared loci have a likelihood value above a set threshold are aggregated together (providing the allele values are the same). The Minimum Likelihood Threshold sets how low the likelihood can be and still allow a match. This threshold can be set anywhere above $1 \times 10^4$ with a default setting of $1 \times 10^{10}$. All of the STR results must match each other before a sample can be added to an aggregate.

Toggling 'Ignore Allelic Dropouts' on allows a homozygous marker to match with a heterozygous marker as long as the homozygous allele has a match with one of the heterozygous alleles for that locus. This allows for allelic dropout of degraded samples when forming the aggregates. In the example shown in FIGS. 1A–1E above, the data were compared without 'ignoring allelic dropout', therefore, the 13 at locus D16S539 in sample S2-00039-21 counted as a mismatch to the 12/13 heterozygous alleles in the victim samples of aggregate AS009676 at that same locus. If these samples were compared with Ignore Allelic Dropout turned on, then the alleles at this same locus would not have been considered a mismatch.

In one embodiment, the M-FISys comparison algorithm includes the following steps. Initially, all of the scientist's previous decisions are preserved. Samples that have been merged together using the Merge command will be grouped into an aggregate regardless of the match criteria chosen for comparing the STR data. Samples that have already been identified as a Reported Missing person through any modality, both by DNA evidence and through non-DNA means, will also be automatically grouped into an aggregate. Samples that cannot meet the chosen match criteria described above are removed from the calculation. The remaining samples are iteratively compared to each existing aggregate. A sample that does not match any existing aggregate becomes a new aggregate itself and the comparison begins again until all of the samples are contained within aggregates, even if they are the only member.

Once all of the samples have been assigned to aggregates, the comparison begins again by comparing all of the aggregates to each other and combining/merging matching aggregates together. Each aggregate can be represented by a single STR profile that is a composite of all the substituent profiles in the aggregate. If alleles are available in one member of the aggregate but not in others, the composite profile will be made up of the non-conflicting information at each marker location from any of the individual samples that make up that aggregate. A composite profile made up of several different samples which might or might not ultimately prove to have come from the same individual, is different from a Virtual Profile, where multiple tests are performed upon the same biological sample and the partial results from each attempt are combined. In one embodiment, for the purpose of comparison, each sample's STR profile is represented by a calculated hexadecimal signature to facilitate comparing large numbers of STR profiles (10,000s) to each other.

Figure 2:
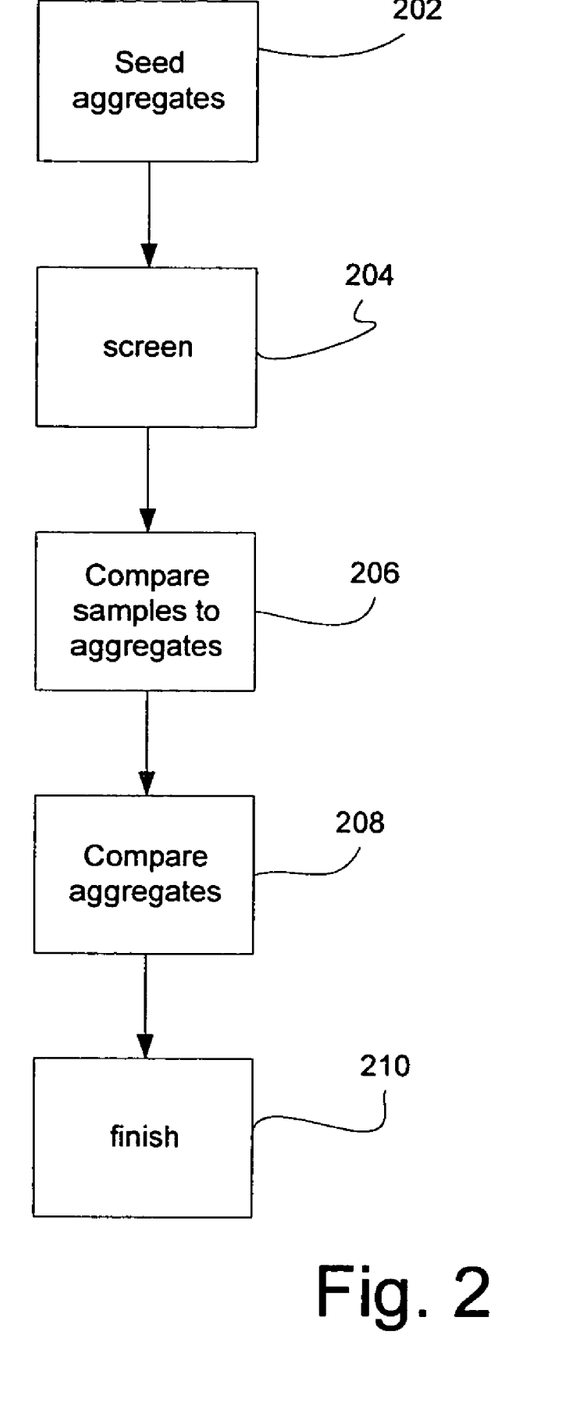
FIG. 2 illustrates a method of comparing sample data in one embodiment.

FIG. 2 illustrates a method of comparing sample data in one embodiment. An aggregate refers to a logical 'container' holding one or more DNA profiles derived from DNA-bearing forensic items. Aggregates most commonly contain DNA profiles, which have been grouped together using user-specified matching criteria, but may also contain DNA profiles included at the sole discretion of the user, for example, because non-DNA evidence dictates such a grouping. In one embodiment, all DNA profiles in an aggregate are of a common type, for example STR profiles or SNP profiles, and each profile in an aggregate contributes to a single composite profile which is representative of an aggregate's contents. Each aggregate also has a single signature derived from the composite profile. While several aggregates may share the same signature, the composite profile will be unique, given the matching criteria in use.

The term 'sample' is commonly used to refer to the DNA profile of a single forensic item. An aggregates may contain a single sample, and thus have a single profile and a single signature. The aggregation process forms a set of aggregates containing different numbers of DNA profiles, as will be described with reference to FIGS. 2 and 3. In one embodiment, the aggregation process includes two phases: the first phase generates aggregates including those that may be subsets of other aggregates; the second phase includes comparing the aggregates in order to merge those that are subsets of another. This is achieved by comparing aggregates to each other—those being compared are referred to as "Candidate" aggregates, those to which they are compared are referred to as "Target" aggregates. All aggregates start as Candidates and are compared to Targets, and will either be merged with an existing Target aggregate, or will join the list of Target aggregates for other Candidates to be compared to. The process of 'binning' reduces the number of comparisons necessary at this phase.

Referring to FIG. 2, at 202, aggregates are created. Aggregates may be created, for example, from user Merge commands. Any samples that have been manually merged together are preserved as aggregated samples. Aggregates may also be created from identifications, for example, samples that have been identified as belonging to the same person are aggregated together. Subset aggregates that are redundant may be removed.

Further, there may be some RMs from which the users have excluded victim samples. For example, a forensic scientist may have manually indicated that "whether or not the identity of the victim that contributed this sample is known, it is known that this sample did not come from this particular RM." Those excluded victim samples and the reference samples associated with the aforementioned RMs are each added as aggregates containing only a single sample.

At 204, all samples and aggregates that are not valid match candidates are removed. If a sample cannot meet the match criteria, for example, the sample has 10 loci, and the comparison criteria have been set to require 11, then it is not a valid match candidate.

At 206, samples are put into all aggregates that have matching STR profiles. If no matches are found for a sample, a new aggregate is made for that sample. Subsequent samples may be compared to this newly created aggregate.

At 208, all aggregates with matching profiles are combined together. At 210, the new aggregates and the invalid samples and the aggregates that were removed at 204 are combined to form the Master List.

A valid match candidate is an STR profile of a sample or aggregate that meets the minimum requirements for being a valid match, as specified by the comparison criteria. If the comparison method being used is Match Count, then the profile must have at least as many markers as the required match count, since it would otherwise be impossible to have N matching markers if the profile contains fewer than N markers. If the comparison method being used is likelihood-based, then the profile's likelihood need to be at least the minimum required likelihood, since due to the way that the likelihood of the intersection of two profiles is calculated, the likelihood of the intersecting markers can be no greater than the lowest (most common) likelihood of the two profiles.

Figure 3:
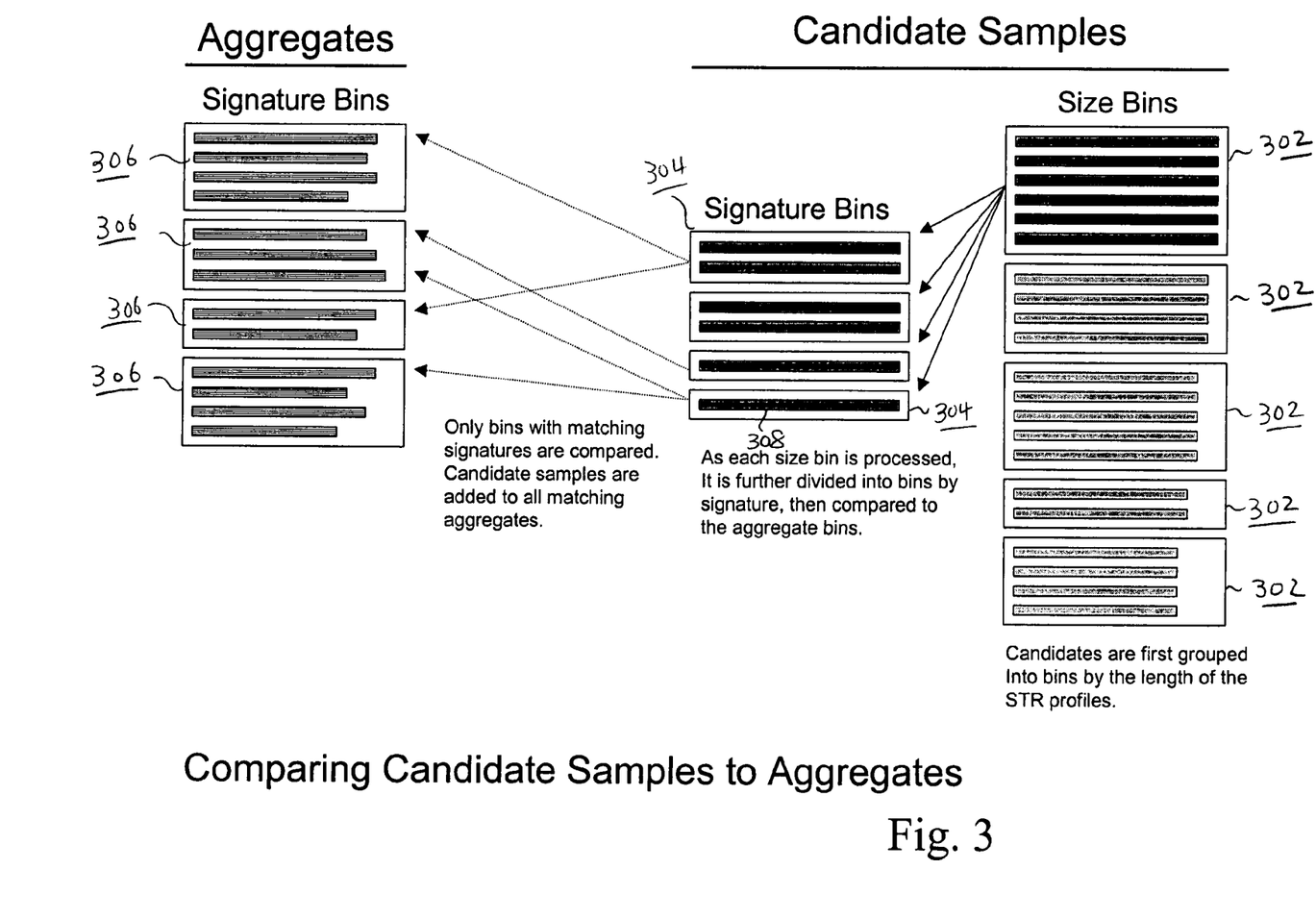
FIG. 3 is a block diagram that illustrates comparing candidate samples to aggregates in one embodiment.

FIG. 3 is a block diagram that illustrates comparing candidate samples to aggregates in one embodiment. This procedure may be used, for example, at step 206 of FIG. 2 to allocate samples into all aggregates that have matching STR profiles. Candidates are first grouped into bins 302 by the length of the STR profiles. The length of an STR profile refers to the number of loci that have available allele values. As each size bin 302 is processed, it is further divided into bins by signature 304, then compared to the aggregate bins 306. Only bins with matching signature are compared. Candidate samples are added to all aggregates with matching profiles within the signature bin.

Figure 4:
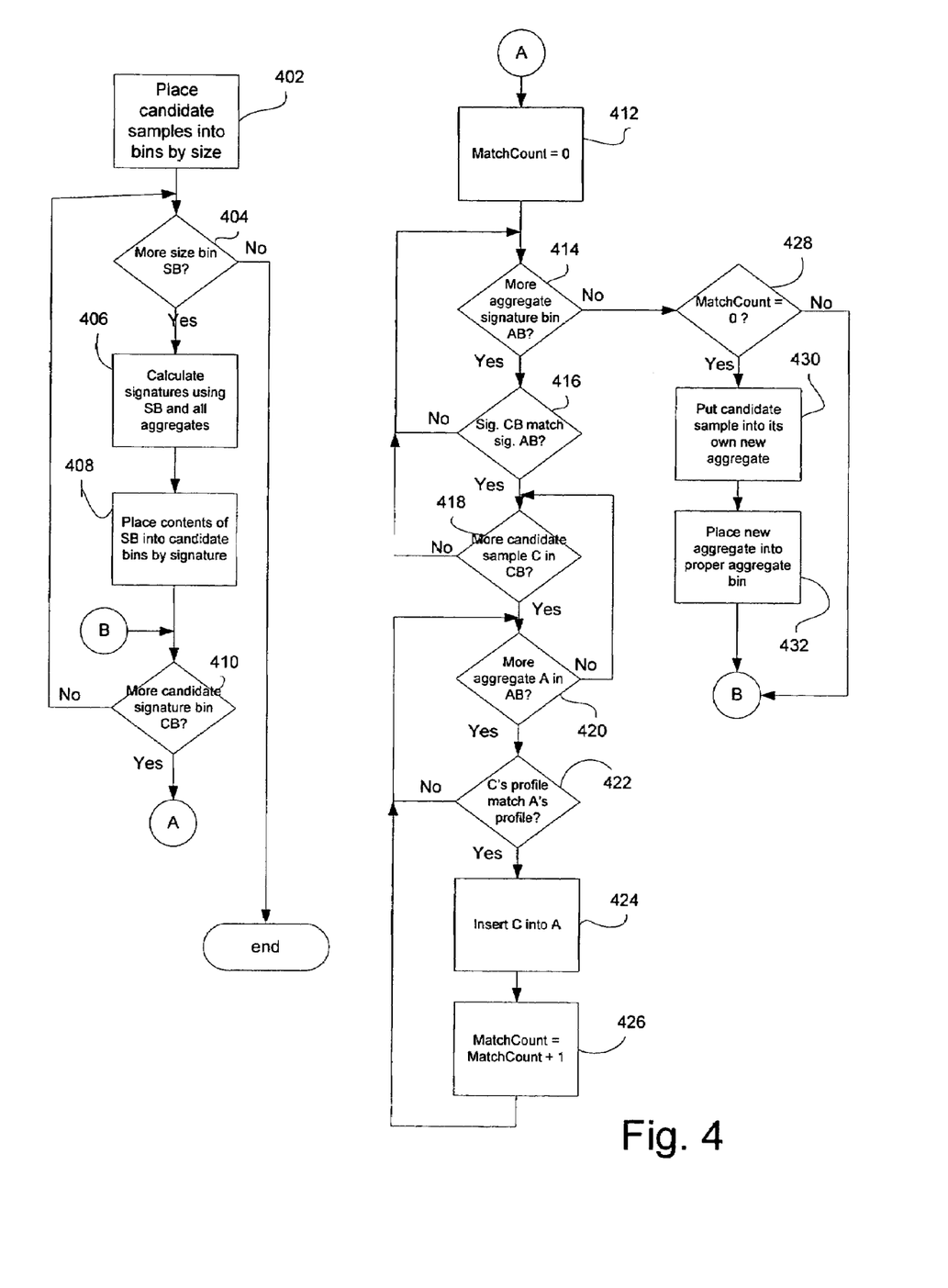
FIG. 4 is a flow diagram illustrating a method of comparing candidate samples to aggregates in one embodiment.

FIG. 4 is a flow diagram that illustrates comparing candidate samples to aggregates in one embodiment. At 402, candidate samples are placed into bins by size. At 404, for each size bin SB (FIG. 3 302), for example, in order of descending size, steps 406 to 432 are performed. At 406, signatures using SB and all aggregates are calculated, as are signatures for all aggregates. Aggregates are then grouped into aggregate signature bins (FIG. 3, 306) by signature. At 408, contents of CB are placed into candidate bins by signature (FIG. 3 304).

At 410, for each candidate signature bin CB (FIG. 3 304), steps 412 to 432 are performed. At 412, a counter, MatchCount is set to zero. At 414, for each aggregate signature bin AB (FIG. 3 306), steps 416 to 426 are performed. At 418, for each candidate sample C (FIG. 3 308) in CB (FIG. 3 304), steps 420 to 426 are performed. At 420, for each aggregate A in AB (FIG. 3 306), steps 422 to 426 are performed. At 422, if C's profile matches A's profile, C is inserted into A at 424 and MatchCount is incremented by one at 426.

At 428, if MatchCount is zero, meaning that this signature C (FIG. 3 308) from SB (FIG. 3 304) did not match with any existing aggregates, the candidate sample is put into its own new aggregate at 430 and the new aggregate is placed into the proper aggregate signature bin at 432.

At this point, in one embodiment, it is possible that some aggregates might match each other, for example, due to the filling in of loci in an aggregate's profile by its members. As a result, it may be necessary to compare aggregates to each other. In this embodiment, the list of aggregates may be duplicated. One copy of the duplicated aggregates is treated as the target aggregates, that is, the aggregates to be added to (for example, as the aggregates at steps 204–206). The second copy of the list is treated as candidate aggregates, that is, aggregates to be added (analogous to the candidate samples at steps 204–206), that is, candidate aggregates. These are still aggregates, but are treated as potential matches to other aggregates.

Figure 5:
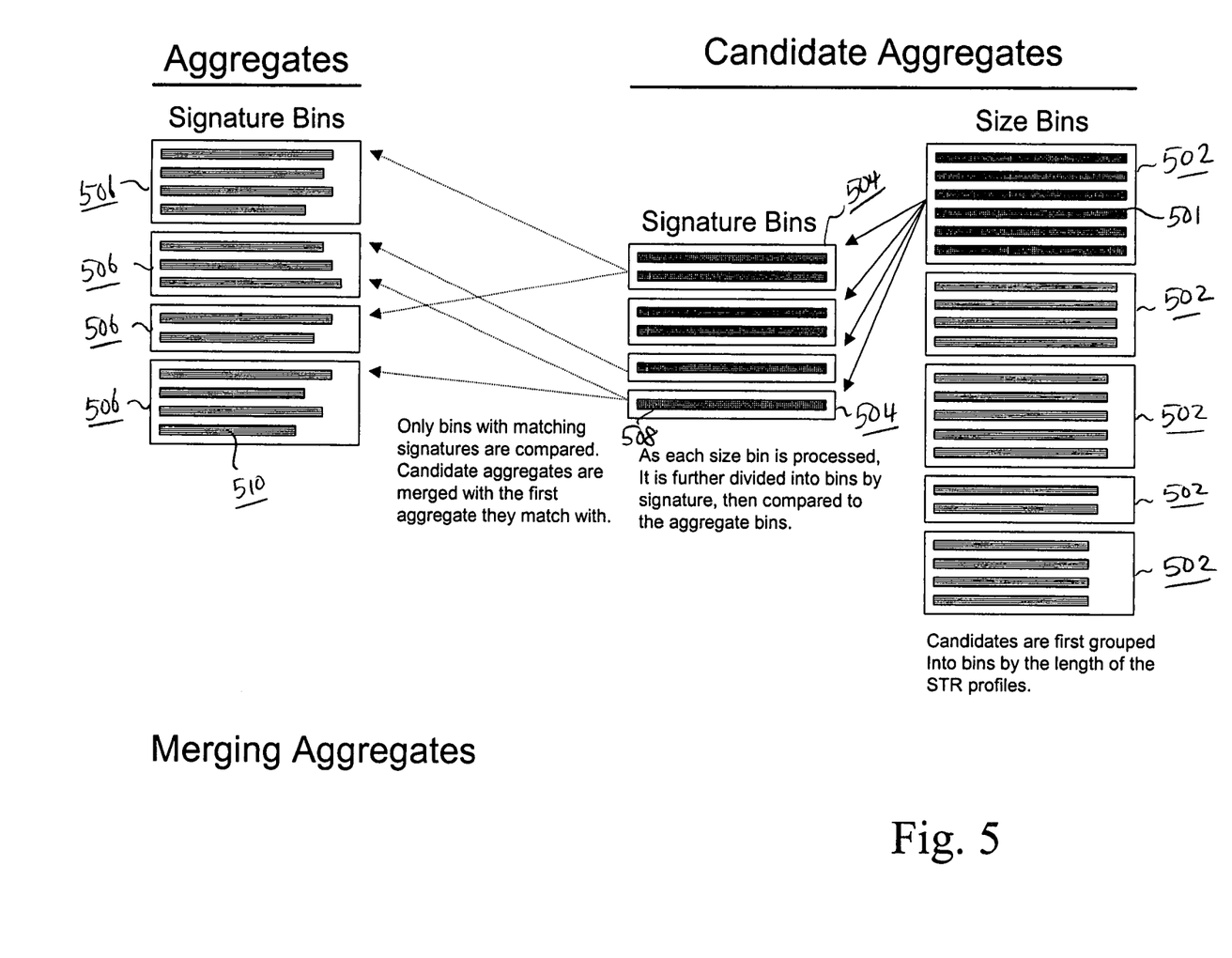
FIG. 5 is a block diagram that illustrates comparing and combining, for example, merging aggregates in one embodiment.

FIG. 5 is a block diagram that illustrates comparing and combining, for example, merging aggregates in one embodiment. This procedure may be used, for example, at step 208 of FIG. 2 to combine all aggregates with matching profiles together. Candidate aggregates, for example, 501, are grouped into bins 502 by the length of the STR profile. An aggregate (for example, 501) is a group of one or more samples that share some similarity, for example, samples that have selected matching criteria. A candidate aggregate 501 containing a number of samples may be merged into another aggregate (target aggregate), which also may contain a number of samples.

Candidate aggregates, for example, 501, are grouped into bins 502 by the length of the STR profile. As each size bin SB 502 is processed, it is further divided into candidate aggregate bins by signature (CAB) 504, then compared to the target aggregate bin 506. In one aspect, only bins with matching signatures are compared. Candidate aggregates are merged with each aggregate that matches.

Figure 6:
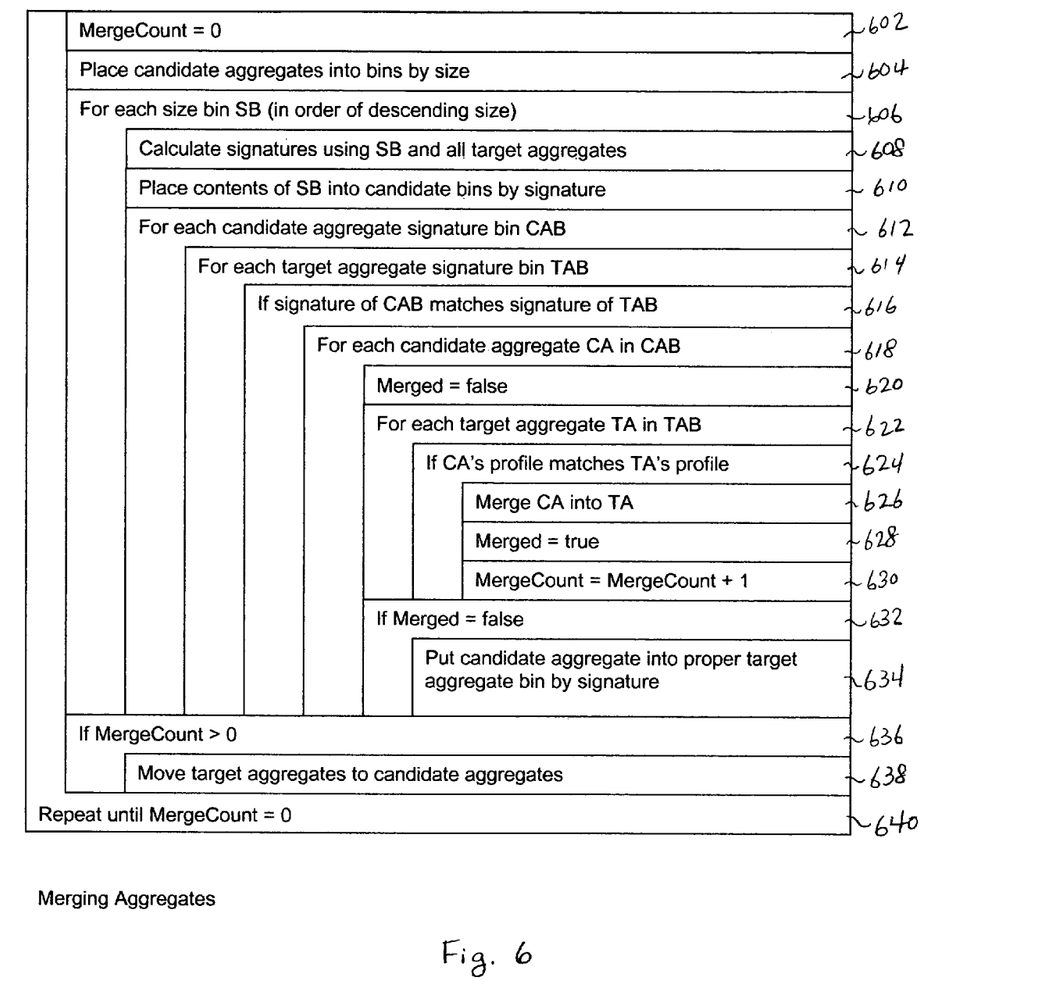
FIG. 6 is a flow diagram illustrating a method of comparing and combining, for example, merging aggregates in one embodiment.

FIG. 6 is a flow diagram illustrating a method of comparing and combining, for example, merging aggregates in one embodiment. At 602, a counter, for example, MergeCount, is initialized and set to zero. At 604, candidate aggregates are placed into bins by size. At 606, for each size bin SB (FIG. 5, 502), for example, in order of descending size, steps 608 to 634 are performed.

At 608, the signatures of all aggregates in SB (FIG. 5, 501) and all target aggregates are calculated (FIG. 5, 506). Target aggregates are then grouped by signature into target aggregate signature bins (TAB). In one embodiment, target aggregates include the entire aggregate list. At 610, contents of SB (FIG. 5, 501) are placed into candidate bins by signature (FIG. 5, 504). At 612, for each candidate aggregate signature bin CAB (FIG. 5, 504), steps 614 to 634 are performed.

At 614, for each target aggregate signature bin TAB (FIG. 5, 506), steps 616 to 634 are performed. At 616, if signature of candidate aggregate bin CAB (FIG. 5, 504) matches signature of TAB (FIG. 5, 506), the contents of these bins are compared. In one embodiment, all aggregates in each candidate aggregate bin CAB have the same signature, and the CAB is represented by this signature. TAB also is represented by a signature and all aggregates contained in a TAB have the same signature. At 618, for each candidate aggregate CA (FIG. 5, 508) in CAB (FIG. 5, 504), steps 620 to 634 are performed. At 620, a merged flag is initialized to false. At 622, for each target aggregate TA (FIG. 5, 510) in TAB (FIG. 5, 506), steps 624 to 630 are performed.

In one embodiment, each candidate aggregate in candidate aggregate bin CAB has one profile associated with it. At 624, if CA's (FIG. 5, 508) profile matches TA's (FIG. 5, 510) profile, CA is merged into TA at 626, that is, samples in CA are moved into TA. At 628, Merged flag is set to true. At 630, MergeCount is incremented by one.

At 632, alternatively, if Merged flag is set to false, then, at 634, the candidate aggregate becomes a new member of the target aggregate's TAB rather than merging with the target aggregate, meaning that while the profiles of the candidate aggregate and the target aggregate do not match, their respective signatures are the same and therefore the CA is added to the TAB with the same signature.

At 636, if MergeCount is greater than zero, at 638, target aggregates are duplicated as candidate aggregates for the next round of comparison. At 640, the steps 602 to 638 are repeated until MergeCount is zero, meaning that no candidate aggregates are merged with target aggregates and therefore, no change in the membership of target aggregates has occurred and there is no need for another round of comparison between CA and TA sets.

STR profile signatures are used to cluster STR profiles. Clustering is done to reduce the $O(N^2)$ penalty when trying to aggregate all profiles together by comparing them to each other. An STR profile signature is a balance between specificity and clustering ability. If there is too much information (too much specificity) then the clusters will be too fine-grained. At the extreme, each unique profile will be its own cluster, and the $O(N^2)$ penalty will not be reduced. At the other extreme, if there is too little information, then the clusters will be too large, and again, the $O(N^2)$ penalty will occur.

A Signature Calculator is prepared for a given STR profile data set by examining all of the loci for the profiles. In one embodiment, four of the "best" representative loci are selected, and will be used to calculate all signatures for the data set. In this embodiment, normalized allele values are stored in four bits, and 0x f is used to represent missing data. Therefore, the best loci in a given set of data samples have a range of less than or equal to fifteen between the lowest and highest allele values. In addition to requiring a range of no more than fifteen, this embodiment preferentially chooses loci with the least amount of missing data; ties are broken by choosing the locus with the greatest range.

Figure 7:
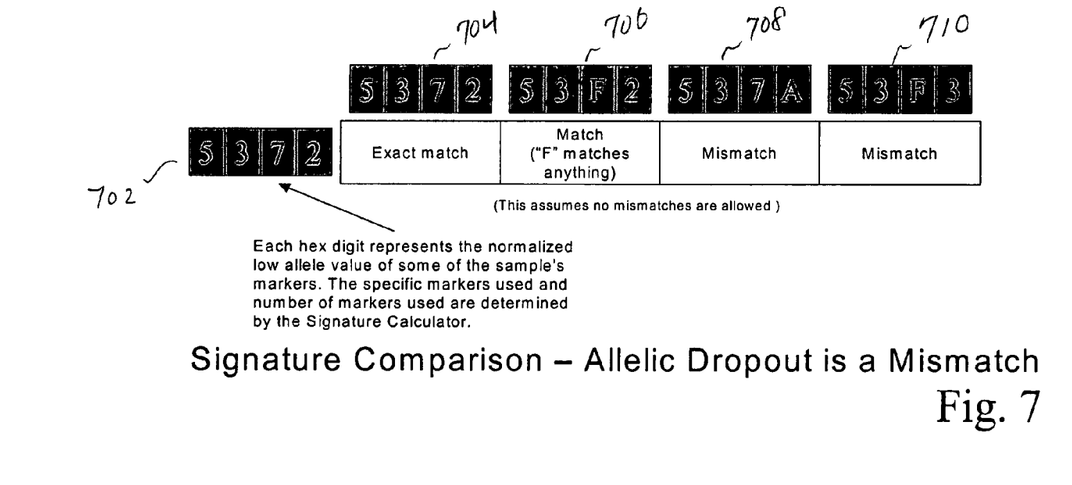
FIG. 7 is a block diagram illustrating signature comparison when allelic dropout is a mismatch.

FIG. 7 is a block diagram illustrating signature comparison when the comparison criteria used indicates that there is a mismatch when there is allelic dropout. For example, when one sample has 7/11 at a particular locus, but another otherwise matching sample has only 7 at that same locus, that is, 11 is missing, the comparison criteria used would indicate a mismatch. If the comparison settings indicate that allelic dropout is a mismatch, the signature is composed of the normalized low allele values for the markers selected by the Signature Calculator. In this application, marker refers to a particular piece of labeled data, like a locus. For example, the value of the alleles at the TPOX locus that are determined in the lab are stored with the TPOX marker in the software that implements the method disclosed. Similarly, a value for a particular SNP is stored at the SNP marker of the same name.

Thus, each hex digit in 702 represents the normalized low allele value of some of the sample's markers. The specific markers used and number of markers used are determined by the Signature Calculator. Two signatures are compared one marker (four bits) 702 704 at a time. If the bits for the marker are different, and one of them is not the value for missing data (0xf) it counts as a mismatch as shown in 708 and 710. If the maximum number of allowable mismatches is exceeded, comparison ceases at that point.

Figure 8:
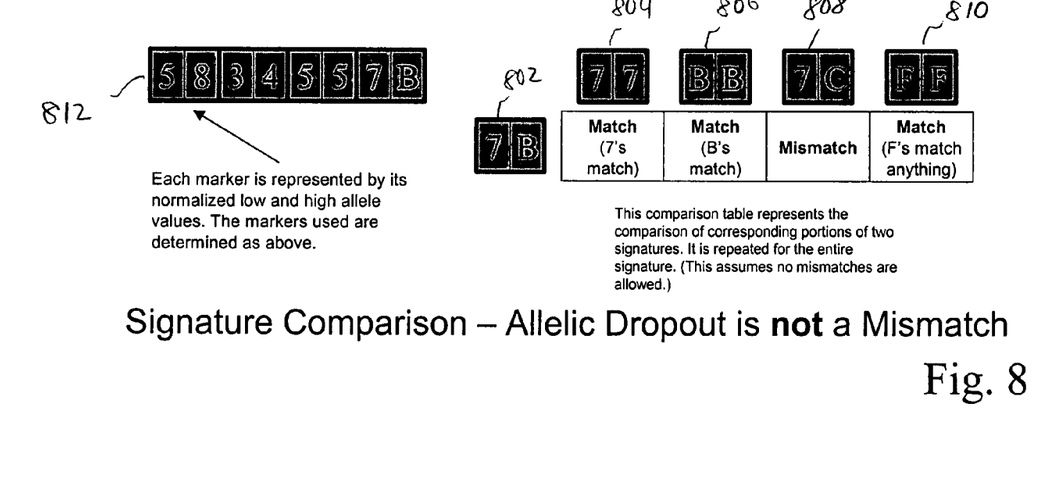
FIG. 8 is a block diagram illustrating signature comparison when allelic dropout is not a mismatch.

FIG. 8 is a block diagram illustrating signature comparison when allelic dropout is not considered as a mismatch. For example, when one sample has 7/11 at a particular locus, but another otherwise matching sample has only 7 at that same locus, a match is made even though 11 is missing.

If the comparison settings indicate that allelic dropout is not a mismatch, the signature 812 is composed of the normalized low and high allele values for the markers selected by the Signature Calculator. Each marker in 812 is represented by its normalized low and high allele values. The two signatures 802 804 are compared one marker (two four-bit alleles) at a time. Mismatches for heterozygous markers or markers with missing data are calculated as described in FIG. 7. If the markers in both signatures are homozygous, they must be identical. If a homozygous marker, for example, as in 804, 806, 810 is being compared with a heterozygous marker 802, it is considered a match if one of the heterozygous alleles matches the homozygous allele value. The comparison table shown 802, 804, 806, and 808 represents the comparison of corresponding portions of two signatures. The comparison is repeated for the entire signature.

Another aspect of the present disclosure involves a difference list representation relating to mitochondrial DNA. As known to those skilled in art, one kind of DNA is referred to as mitochondrial DNA ("mtDNA"). It is not found in the nucleus of the cell but out in the cytoplasm within organelles called mitochondria. Unlike the nuclear DNA that is about 3.5 billion bases long, it is only about 16,569 bases long and comprises very tough material. Thus, it is much more likely to be available in degraded remains, although when the highly variable parts of the mtDNA are sequenced, it is not nearly as specific as nuclear STR values. For example, a full STR profile is expected to be unique such that the chances of two people having the same profile are very small, that is, the probability of a match between profiles of two unrelated persons in a randomly mating population of Caucasian Americans is 1.74×10e-15, or one in 575 trillion. In contrast, the most common pattern in mtDNA is shared by about 7% of the Caucasian population.

In mtDNA, the spelling of the sequence is used instead of the measurement of a length of a DNA sequence. For example, a region of about 600–1,100 bases, depending on a particular laboratory's protocol, is selected and the sequence of these bases is compared to an international standard mtDNA sequence such as the one known as the "Anderson Sequence."

Typically, for identification purposes, the whole string of 600–1,100 characters is not stored. Instead, the current forensic standard is to store a short list of the differences between the sequence being studied and this reference standard, that is the international standard mtDNA sequence.

This short list of the differences, or the difference list is a set of pairs of values, that is, the base position along the mtDNA sequence, and the character that is found to be different from the reference standard. If the sequence being typed is identical to the reference, the difference report will be null. Point mutations are described as a base position, plus the base that differs from the reference sequence. Deletions are typically represented as a "D" character. The difference list is referred to as the "delta representation."

A typical mitotype might look like this:

16093: C
16224: D
16311: C
195: C
263: G
315.1: C

The numbers on the first column represent a position in the DNA sequence. The characters in the second column represent the DNA spelling, the D character representing a delete or missing position. Note that the base positions cross the origin of the 16569-base genome. The first lines indicate that this sample has a C at position 16093 where a T is found in the Anderson sequence, and a deletion of the base found in Anderson at position 16224. To maintain the integrity of numbering, an insert is indicated as a decimal point position on the base that the insert follows. In this case, "315.1: C" indicated that there is a C insert after position 315 in the reference sequence.

At present, there is no one standard for delta representation. For instance, if the reference sequence includes the sequence "TTT" starting at position 16091, and the sample under study has four T's rather than three, it can logically be represented as any of the following:

16090.1: T
16091.1: T
16092.1: T
16093.1: T

Thus, there is more than one way of representing the difference. However, when comparing one "mitotype" pattern to another, they must be represented using the same representation or nomenclature, otherwise a computer program will not recognize the two sequences being compared as identical. For example, comparing the DNA sequence in the above example, "ACTTTTAG" to the same string "ACTTTTAG" should find that they are equal. However, the conventional methods may represent the difference in the first string as occurring at 16090.1 and the difference in the second string as occurring at 16091.1. Accordingly, when these two representations of differences are compared, they are not found identical, even though the strings themselves are identical.

A method provided in the present application, in one aspect, circumvents this existing nomenclature problem by translating the delta representation back to the original string, then comparing the strings. With this novel method, the ambiguity of using different representations is eliminated.

Thus, if the reference sequence, starting at base #16089 is
    ACTTTAG then this reference sequence is used with any of the four representations above to re-create the original sequence, adding an extra T after base #16090, 16091, 16092 or 16093. In each case, the resulting sequence is the same, with four T's instead of 3.
    ACTTTTAG Thus, the nomenclature problem that currently exists in forensic identification procedure is eliminated. Methods for comparing the DNA strings after they have been created as stated are well known, and thus will not be described in this disclosure.

Figure 9:
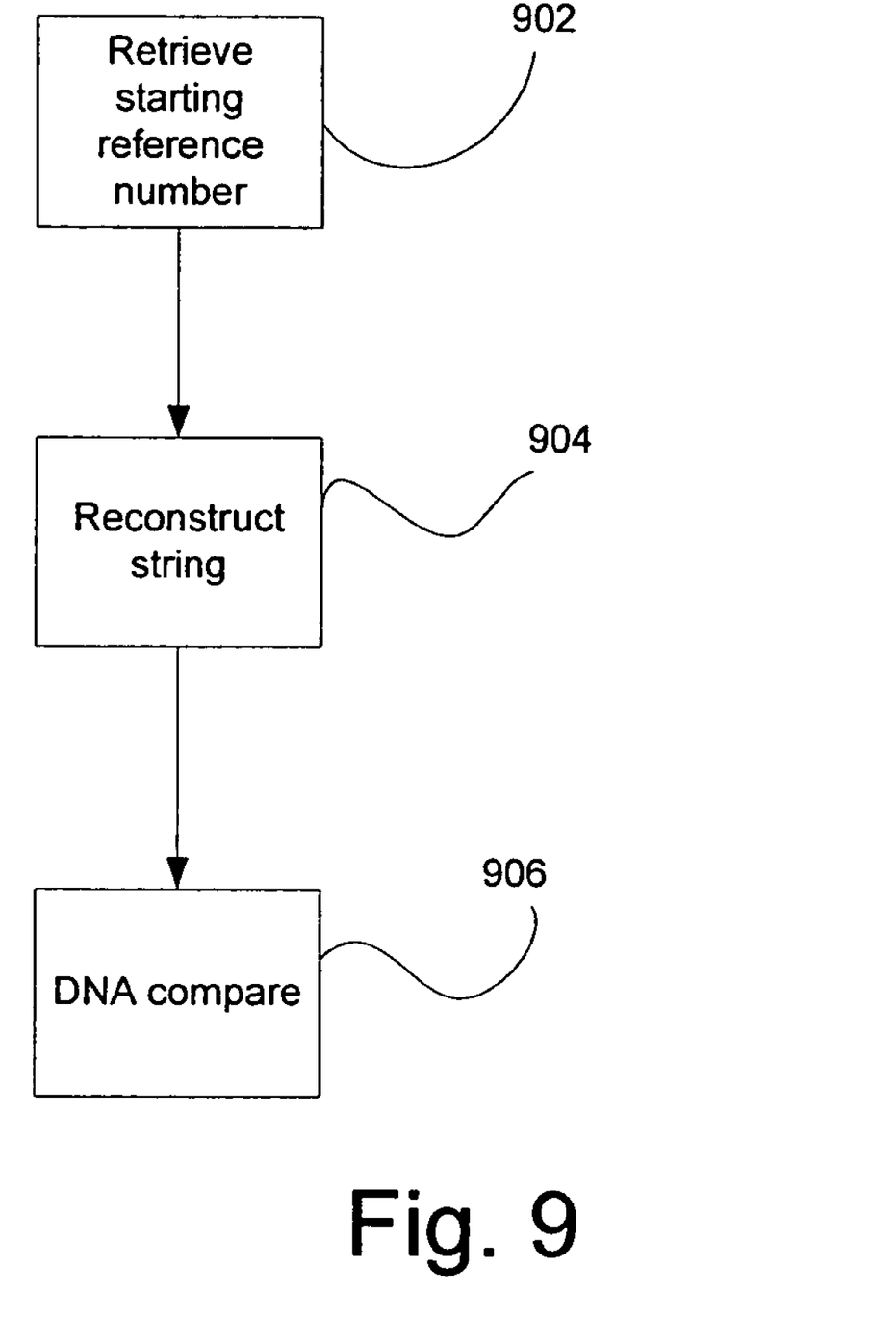
FIG. 9 is a flow diagram illustrating the method of comparing delta representation string of mitochondrial DNA.

FIG. 9 is a flow diagram illustrating the method of comparing delta representation string of mitochondrial DNA. At 902, a reference sequence number beginning the delta representation is retrieved. At 904, original sequence is reconstructed using the Reference sequence and the individual variations from that sequence represented as a position number and the variant at that position. At 906, DNA string comparison is performed using the reconstructed sequence.

In another aspect, the present application discloses a method related to Single Nucleotide Polymorphisms ("SNPs") used for identifying people using DNA and selecting the bases along the genome that are far enough apart to be genetically "unlinked." This involves looking at a series of single bases scattered around the nuclear genome. An existing problem in SNPs is that for kinship studies (that is, comparing the SNP pattern from a person to that of some of his or her blood relatives), to give valid results, the bases have to be far enough apart to be genetically "unlinked." That is, given an arbitrarily dense set of markers along the genome (those markers can be either STR loci or SNP loci) it is important to see that those markers are genetically unlinked if they are to be used for kinship analysis. This requires that the markers be far enough apart (for instance, a genetic distance set by the user such as 50 centiMorgans) so that they are as likely to be inherited together as not to be inherited together. Traditional experimental approaches attempt to identify locations on the genome such that all data collected in the laboratory are at least that minimum distance apart. Following that, computer analysis is guaranteed not to be skewed by using data points that are not independent. This may require long experimental study period to find an appropriate "panel" of markers.

Figure 10:
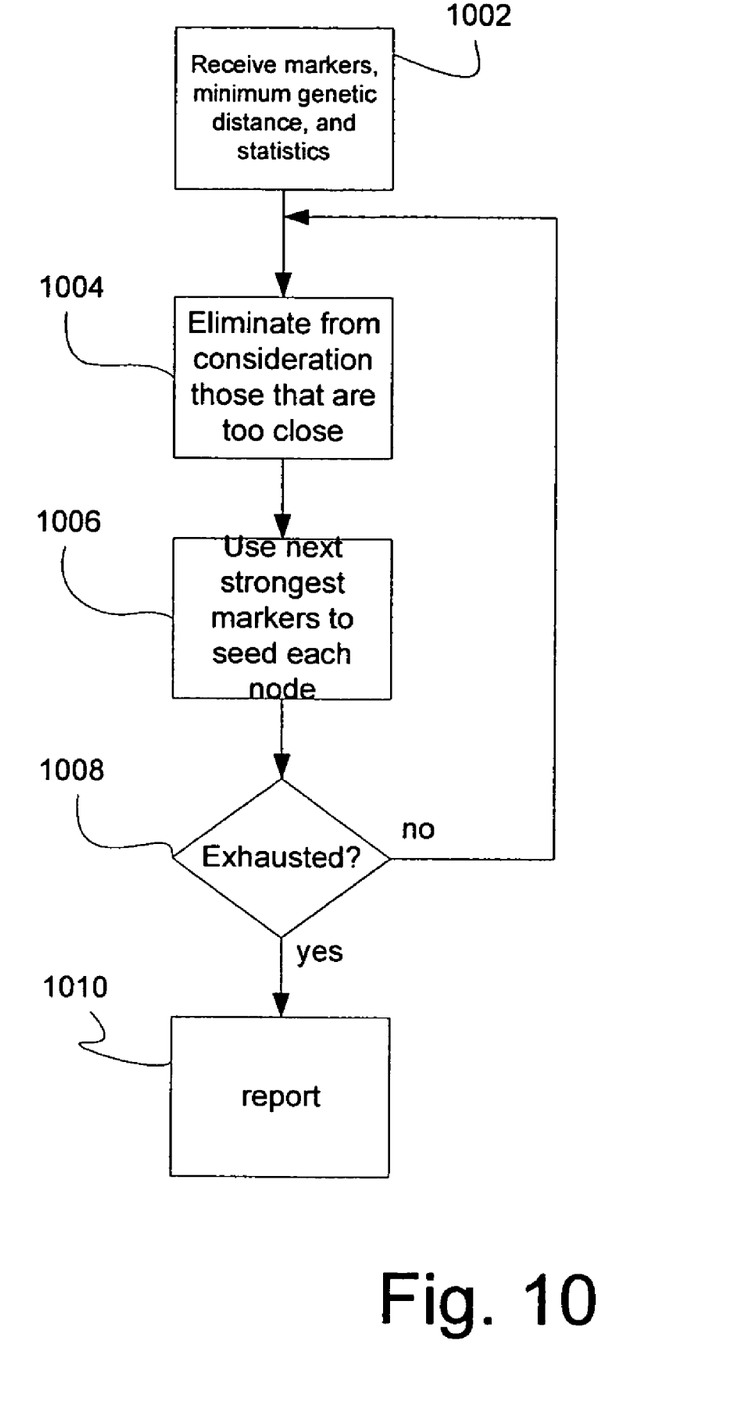
FIG. 10 is flow diagram illustrating a method of selecting a plurality of bases along a single nucleotide polymorphisms (SNP) genome that are far enough apart to be genetically unlinked in one embodiment.

A method provided in the present application in one aspect takes an alternative approach that eliminates the need to carefully select marker locations based on empirical laboratory study of pairwise linkage. FIG. 10 is flow diagram illustrating a method of selecting a plurality of bases along a single nucleotide polymorphisms (SNP) genome that are far enough apart to be genetically unlinked in one embodiment. At 1002, the method takes as input an arbitrary dense panel of markers, along with a minimum genetic distance that is required between markers and a minimum statistical likelihood needed to establish a match.

That minimum likelihood is a policy decision that may be set by a researcher, and is not an absolute value.

The method attempts to select a subset of all the markers available such that the subset meets the required statistical threshold for a match without violating the minimum genetic distance between markers. This method depends on the genetic location of all the markers being known, so that distance between any two can be computed. At 1004, it starts with the individual markers with the highest independent likelihood, masking off, that is, eliminating from consideration, all those markers that are too close to that marker to be genetically unlinked. At 1006, if a group cannot be found that meets the statistical threshold for a match, the next strongest markers, for example, with the highest independent likelihood, are used to seed each node of the decision tree of best markers. This continues until a combination of markers is found that meets both the minimum distance and minimum likelihood threshold, or until all combinations are exhausted. When all combinations are exhausted at 1008, the method at 1010 reports that there is an acceptable combination of markers that meet the proposed parameters.

Another aspect of the present application creates a single program that uses multiple modalities in combination to make identification. That is, STR's, mtDNA and SNP's are all used together, each giving incrementally more evidence in accurately identifying a person. Currently, there exist programs and spreadsheets that perform STR comparison, either directly to references or to kin of the person being identified. There are programs that compare mtDNA patterns. There are software packages for using SNP's to determine genetic characteristics, even if they have never been used in forensic identification before. A method disclosed in the present application in one aspect works for any combination of DNA-based modalities in refuting a tentative identification or providing more confidence in that identification. For example, if one of the methods produces a false or negative result while the other two methods produce a positive result during identification, a tag may be created to indicate that 100% accuracy has not yet been obtained in this particular case. Using these multiple modalities allows the information from one identification method to support or refute a hypothesis based on the other types of identification mode.

The method described herein may be embodied in any software program and implemented, for example, in C# (C-sharp), an object oriented programming language from Microsoft® and may be run on a general purpose or specialized computer systems.

The embodiments described above are illustrative examples and it should not be construed that the present disclosure is limited to these particular embodiments. Thus, various changes and modifications may be effected by one skilled in the art without departing from the spirit or scope of the invention as defined in the appended claims. Accordingly, the present invention is not limited except as by the appended claims.

We claim:

1. A method for profiling and identifying persons by using data samples, comprising:

providing a collapsed list of one or more aggregated matching samples, the matching samples having DNA profiles matched based on one or more selected criteria consistent with all of the matching samples identifying a single individual;

presenting each of the one or more aggregated matching samples on a one-line display, the one-line display having a composite profile representative of all DNA profiles in matching samples that satisfy one or more predetemined comparison criteria; and allowing the one-line display of an aggregated matching sample to be expanded, the expanded one-line display providing a view of all member samples in the aggregated matching sample.

2. The method of claim 1, wherein a member sample may be displayed as a member of more than one aggregated matching sample.

3. The method of claim 2, further including:

marking a view of the member sample that belongs to more than one aggregated matching sample with an ambiguity flag.

4. The method of claim 1, further including:

allowing one or more new samples to be added to one or more aggregated matching samples based on one or more predetermined comparison criteria.

5. The method of claim 1, further including:

allowing one or more new samples to be added to one or more new aggregated matching samples based on one or more predetermined comparison criteria.

6. The method of claim 4, wherein the predetermined comparison criteria include match count criteria, allowed discrepancies criteria, likelihood of shared loci criteria, or ignore allelic dropout criteria, or combination thereof.

7. The method of claim 1, further including:

allowing the one or more aggregated matching samples to be combined based on a predetermined criteria.

8. The method of claim 4, wherein the allowing includes:

grouping the one or more new samples by STR profile length;

determining a signature for each sample in each resulting profile length group;

determining a signature for each existing sample aggregate;
sub-grouping each profile length group by signature into one or more sample sub-groups;
grouping all existing aggregates by signature into one or more aggregate groups;
comparing the signature of each sample sub-group with the signature of each aggregate group;
if the signatures of the compared groups match, comparing the STR profiles of each sample in the sample sub-group with the profile of each aggregate in the matching aggregate group;
if the STR profile of a sample matches that of an aggregate, inserting the sample into the matching aggregate;
if the STR profile of a sample dots not match that of an existing aggregate in the matching aggregate group, creating a new aggregate containing this sample, and making the new aggregate a member of the current matching aggregate group; and
if the signature of a sample sub-group matches no aggregate group, creating a new aggregate group and creating aggregates within the new aggregate group to include the samples in the sample sub-group.

9. The method of claim 7, wherein the allowing includes:
determining a signature of each of-aggregated matching samples;
grouping aggregated matching samples by length of their composite DNA profiles;
sub-grouping each group of one or more aggregated matching samples by signature into candidate aggregate bins;
creating one or more target aggregate bins, each target aggregate bin associated with a unique aggregated matching sample signature;
comparing the signature of each candidate aggregate bin to the signature of each target aggregate bin;
if the signature of the candidate aggregate bin matches the signature of the target aggregate bin, comparing a composite profile of each aggregated matching sample in the candidate aggregate bin with a composite profile of each aggregated matching sample in the target aggregate bin;
if the compared composite profiles match, adding the samples in the matching aggregate matching sample in the candidate aggregate bin to a set of samples in the matching aggregate matching sample in the target aggregate bin; and
if an aggregated matching sample in the candidate aggregate bin has been compared to all aggregates in the matching target aggregate bin and has not been added to an aggregate in the target aggregate bin, adding the aggregated matching sample in the candidate aggregate bin to the target aggregate bin.

10. A program storage device readable by machine, tangibly embodying a program of instructions executable by the machine to perform method of comprising:
providing a collapsed list of one or more aggregated matching samples having DNA profiles matched based on one or more selected criteria that all potentially match a single person;
presenting each of the one or more aggregated matching samples on a one-line display, the one-line display having a composite profile representing representative of all DNA profiles in the matching samples that meet one or more predetermined comparison criteria; and
allowing the one-line display of an aggregated matching sample to be expanded, the expanded one-line display providing a view of all member samples in the aggregated matching sample.

11. The program storage device of claim 10, further including:
providing a virtual profile for a sample.

12. The program storage device of claim 10, further including:
taking one or more results from each experimental attempt where multiple assays are performed upon a single sample; and
building a virtual profile of the sample, the virtual profile represendng the one or more results combined from said each experimental attempt.

13. The program storage device of claim 12, further including displaying the virtual profile under the aggregated matching sample.

14. The program storage device of claim 12, further including:
displaying the virtual profile as a member of one or more aggregates of matching samples;
presenting the virtual profile on a one-line display, the one-line display having a virtual profile sample that is representative of combined results of said each experimental attempt on a single sample; and
allowing the one-line display of the virtual profile to be expanded, the expanded display providing a view of all profile results from said each experimental attempt on a single sample.

15. The method of claim 1, further including:
providing a virtual profile for a sample.

16. The method of claim 1, further including:
taking a plurality of assays on a sample; and
building a virtual profile of the sample using a plurality of results from the plurality of assays.

17. The method of claim 15, further including displaying the virtual profile under the aggregated matching sample.

* * * * *